(12) United States Patent
Vickers et al.

(10) Patent No.: US 10,709,814 B2
(45) Date of Patent: Jul. 14, 2020

(54) OSTEOIMPLANT COMPRISING AN INSOLUBLE FIBROUS POLYMER

(71) Applicant: Warsaw Orthopedic, Inc., Warsaw, IN (US)

(72) Inventors: Scott M Vickers, Hernando, MS (US); Jeffrey L Scifert, Arlington, TN (US); Mirian Gillissen, Gulpen (NL); Didier Billy, Maastricht (NL)

(73) Assignee: Warsaw Orthopedic, Inc., Warsaw, IN (US)

( * ) Notice: Subject to any disclaimer, the term of this patent is extended or adjusted under 35 U.S.C. 154(b) by 29 days.

(21) Appl. No.: 15/135,997

(22) Filed: Apr. 22, 2016

(65) Prior Publication Data

US 2017/0304502 A1     Oct. 26, 2017

(51) Int. Cl.
| | |
|---|---|
| *A61L 27/46* | (2006.01) |
| *A61L 27/24* | (2006.01) |
| *A61L 27/26* | (2006.01) |
| *A61L 27/50* | (2006.01) |
| *A61L 27/54* | (2006.01) |
| *B29B 7/00* | (2006.01) |
| *B29K 309/02* | (2006.01) |
| *B29L 31/00* | (2006.01) |

(52) U.S. Cl.
CPC .............. *A61L 27/46* (2013.01); *A61L 27/24* (2013.01); *A61L 27/26* (2013.01); *A61L 27/50* (2013.01); *A61L 27/54* (2013.01); *B29B 7/00* (2013.01); *A61L 2430/02* (2013.01); *B29K 2005/00* (2013.01); *B29K 2089/00* (2013.01); *B29K 2309/02* (2013.01); *B29L 2031/7532* (2013.01)

(58) Field of Classification Search
None
See application file for complete search history.

(56) References Cited

U.S. PATENT DOCUMENTS

| | | | | |
|---|---|---|---|---|
| 5,326,350 | A | * | 7/1994 | Li ..................... A61B 17/0057 |
| | | | | 128/DIG. 8 |
| 5,986,168 | A | | 11/1999 | Noishiki |
| 6,090,996 | A | * | 7/2000 | Li ........................ A61L 31/148 |
| | | | | 606/151 |
| 7,214,765 | B2 | | 5/2007 | Ringeisen et al. |
| 7,910,690 | B2 | | 3/2011 | Ringeisen et al. |
| 7,939,092 | B2 | | 5/2011 | McKay et al. |
| 8,188,229 | B2 | | 5/2012 | Ringeisen et al. |
| 8,840,913 | B2 | | 9/2014 | McKay et al. |
| 9,211,359 | B2 | | 12/2015 | McKay et al. |

(Continued)

OTHER PUBLICATIONS

International Search Report and Written Opinion for PCT/2017/028802, the counterpart application dated Sep. 5, 2017, 13 pages.

(Continued)

*Primary Examiner* — Carlos A Azpuru
*Assistant Examiner* — Casey S Hagopian (57) ABSTRACT

Methods for making an osteoimplant are provided. In one embodiment the method includes applying a mechanical force to an aqueous slurry of insoluble collagen fibers to entangle the insoluble collagen fibers so as to form a semi-solid mass of entangled insoluble collagen fibers; and lyophilizing the semi-solid mass of entangled collagen fibers to form the osteoimplant. An osteoimplant containing entangled insoluble collagen fibers is also provided.

9 Claims, 3 Drawing Sheets

(56) References Cited

U.S. PATENT DOCUMENTS

| | | | |
|---|---|---|---|
| 2008/0031914 A1 | 2/2008 | Drapeau et al. | |
| 2008/0152691 A1 | 6/2008 | Drapeau et al. | |
| 2009/0246244 A1* | 10/2009 | McKay | A61L 27/26 |
| | | | 424/423 |
| 2011/0276147 A1* | 11/2011 | Cook | A61L 27/46 |
| | | | 623/23.51 |
| 2012/0107401 A1 | 5/2012 | McKay | |
| 2012/0164225 A1* | 6/2012 | Cook | A61L 27/46 |
| | | | 424/484 |
| 2012/0207839 A1 | 8/2012 | Liu et al. | |
| 2014/0287014 A1 | 9/2014 | Ringeisen et al. | |
| 2014/0303744 A1* | 10/2014 | Evans | A61L 27/12 |
| | | | 623/23.51 |
| 2014/0341964 A1* | 11/2014 | McKay | A61L 24/0084 |
| | | | 424/423 |
| 2015/0306276 A1 | 10/2015 | Shimp | |

OTHER PUBLICATIONS

Extended European Search Report dated Nov. 22, 2019 issued by the European Patent Office in European Appl. 17786701.7 filed Apr. 21, 2017 for An Osteoimplant Comprising an Insoluble Fibrous Polymer.

* cited by examiner

OSTEOIMPLANT COMPRISING AN INSOLUBLE FIBROUS POLYMER

BACKGROUND

The present disclosure relates generally to medical implant materials, and in certain aspects to medical putty implant materials containing insoluble biodegradable polymers and, optionally, other components.

A variety of materials have been suggested for the treatment of bone defects. In addition to traditional bone grafting, a number of synthetic bone graft substitutes have been used or explored, including several putty materials.

To regrow bone effectively, implant materials derive benefit from the presence of substantial scaffolding material such as biocompatible ceramics or other mineral scaffolds. Such mineral materials are generally hard, brittle substances. The incorporation of substantial levels of mineral particles into putty materials, particularly granules or other relatively large partides, proves difficult because the large pieces of hard mineral tend to disrupt the putty mass such that it is readily broken or eroded away, and lacks the cohesiveness desired for handling prior to implant and for persistence after osteoimplant is implanted at the target bone tissue site. This may present problems in achieving effective bone growth into and through the desired implant volume, due to migration or separation of the scaffolding particulates.

There exists, therefore, a need for improved putty materials which have incorporated mineral particles While maintaining the desired combination of malleability and cohesiveness. In certain aspects, the present disclosure is directed to these needs.

SUMMARY

Methods for making an osteoimplant material are provided. In one embodiment, the method includes applying a mechanical force to an aqueous slurry of insoluble collagen fibers to entangle the insoluble collagen fibers so as to form a semi-solid mass of entangled insoluble collagen fibers; and lyophilizing the semi-solid mass of entangled collagen fibers to form the osteoimplant. In some embodiments, the mechanical force can be provided by a grinder or an IKA blender. The insoluble collagen fibers can be crosslinked or non-crosslinked. In some aspects, the crosslinking of the insoluble collagen can occur prior to lyophilization.

In various aspects in order to obtain an insoluble collagen osteoimplant having enhanced characteristics, for example, osteoconductivity, enhanced compression resistance, improved handling properties, the semi-solid mass of entangled insoluble collagen fibers can further include other components. Additional components that can be added to the osteoimplant of entangled insoluble collagen fibers include ceramic granules, which can provide enhanced osteoconductivity and compression resistance, starch or alginate which can provide enhanced handling characteristics, and polyethylene glycol, which acts as a hydration agent. In some aspects, when the semi-solid mass of entangled insoluble collagen fibers includes other additional components, the amount of purified fibrillary collagen can vary from 1% to 12.5% by weight of the entangled insoluble collagen fibers osteoimplant.

In some embodiments, the ceramic granules can be biphasic calcium phosphate in an amount from about 1% to about 75% by weight and comprise tricalcium phosphate and hydroxyapatite in a ratio from about 40:60, 50:50 to about 95:5. The ceramic granules can have an average particle size form about 0.5 to about 1.6 mm, in some aspects.

In other embodiments, polysaccharides such as starch or alginate can be added to the semi-solid mass of entangled insoluble collagen fibers. The amount of polysaccharide can vary from about 0.1% to about 12.5% by weight based on the weight of the entangled insoluble collagen fibers.

Polyethylene glycol, a hydrating agent, can be added to the semi-solid mass of entangled insoluble collagen fibers, in other aspects. The amount of hydrating agent can vary from about 0.01% to about 1.5% by weight based on the weight of the entangled insoluble collagen fibers.

The resulting insoluble collagen osteoimplant can be fashioned into implants for filling osseous voids and for promoting fusion of osseous tissues. In some embodiments, the osteoimplant described in this application comprises entangled insoluble collagen fibers from 75% to 100% by weight based on the total weight of the osteoimplant. The osteoimplant can be provided in a pre-hydrated, ready-to-use formulation, or can be lyophilized and subsequently hydrated with bone marrow, blood, physiological saline, sodium chloride, dextrose, Lactated Ringer's solution, phosphate buffer solution (PBS), bone marrow fractions or a combination thereof.

The present application also provides an osteoimplant comprising entangled insoluble collagen fibers that can be used for delivery of a bioactive agent. In certain embodiments, a bioactive agent can be delivered with the entangled fibers of the insoluble collagen implant, the bioactive agent comprising a growth factor, a bone morphogenetic protein, an analgesic, an anti-inflammatory, and antibiotic, a cytokine, a chemotherapeutic or a mixture thereof. In some embodiments, the bone morphogenetic protein bound to the entangled fibers of the insoluble collagen implant can be BMP-2.

In other embodiments, the methods described herein contemplate further adding to the osteoimplant, an osteoinductive additive comprising bone marrow aspirate, blood, blood products, synthetic and naturally-derived bone morphogenic proteins, growth factors, particulate demineralized bone matrix, or mixtures thereof. In other embodiments, the methods described herein contemplate further adding an osteoconductive additive, the osteoconductive additive comprising calcium phosphates, calcium sulfate, particulate demineralized bone matrix, naturally-derived allogenic bone mineral, naturally-derived autogenic bone mineral or mixtures thereof.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits and advantages of the embodiments will be apparent with regard to the following description, appended claims and accompanying drawings where:

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/− 10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

"Bioactive agent" or "bioactive compound" is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In certain embodiments, the bioactive agent is a small molecule. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD peptides.

A more complete listing of bioactive agents and specific drugs suitable for use in the present application may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996; and the United States Pharmacopeia-25/National Formulary-20, published by the United States Pharmacopeia Convention, Inc., Rockville Md., 2001, and the "Pharmazeutische Wirkstoffe", edited by Von Keemann et al., Stuttgart/New York, 1987, all of which are incorporated herein by reference. Drugs for human use listed by the U.S. Food and Drug Administration (FDA) under 21 C.F.R. §§ 330.5, 331 through 361, and 440 through 460, and drugs for veterinary use listed by the FDA under 21 C.F.R. §§ 500 through 589, all of which are incorporated herein by reference, are also considered acceptable for use in accordance with the present disclosure.

"Biodegradable", "bioerodable", or "resorbable" materials are materials that degrade under physiological conditions to form a product that can be metabolized or excreted without damage to the subject. In certain embodiments, the product is metabolized or excreted without permanent damage to the subject. Biodegradable materials may be hydrolytically degradable, may require cellular and/or enzymatic action to fully degrade, or both. Biodegradable materials also include materials that are broken down within cells. Degradation may occur by hydrolysis, enzymatic processes, phagocytosis, or other processes.

"Biocompatible," as used herein, is intended to describe materials that, upon administration in vivo, do not induce undesirable long-term effects.

"Bone," as used herein, refers to bone that is cortical, cancellous or cortico-cancellous of autogenous, allogenic, xenogenic, or transgenic origin.

"Demineralized," as used herein, refers to any material generated by removing mineral material from tissue, for example, bone tissue. In certain embodiments, the demineralized compositions described herein include preparations containing less than 5% calcium. "Demineralized" is intended to encompass such expressions as "substantially demineralized," "partially demineralized," "surface demineralized," and "fully demineralized." "Partially demineralized" is intended to encompass "surface demineralized."

"Demineralized bone activity" refers to the osteoinductive activity of demineralized bone.

"Demineralized bone matrix (DBM)," as used herein, refers to any material generated by removing mineral material from bone tissue. In some embodiments, the DBM compositions as used herein include preparations containing less than 5% calcium and, in some embodiments, less than 1% calcium by weight. In other embodiments, the DBM compositions comprise partially demineralized bone (e.g., preparations with greater than 5% calcium by weight but containing less than 100% of the original starting amount of calcium).

The term "lyophilized" or "freeze-dried" includes a state of a substance that has been subjected to a drying procedure such as lyophilization, where at least 50% of moisture has been removed. The osteoimplant may be lyophilized or freeze-dried.

"Mammal," as used herein refers to organisms from the taxonomy class "mammalian," including but not limited to humans, other primates such as chimpanzees, apes, orangutans and monkeys, rats, mice, cats, dogs, cows, or horses.

"Osteoconductive," as used herein, refers to the ability of a substance to serve as a template or substance along which bone may grow. In some embodiments, the osteoimplant is osteoconductive.

"Osteogenic," as used herein, refers to materials containing living cells capable of differentiation into bone tissue. In some embodiments, the osteoimplant is osteogenic.

"Osteoimplant," as used herein, refers to any implant prepared in accordance with the embodiments described herein and therefore may include expressions such as bone material, bone membrane, or bone graft. The osteoimplant of the present application is configured to be implanted into a bone cavity.

"Osteoinductive," as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally osteoinductivity may also be scored at later time points such as 40, 60, or even 100 days following implantation. Percentage of osteoinductivity refers to an osteoinductivity score at a given time point expressed as a percentage of activity, of a specified reference score. Osteoinductivity may be assessed in an athymic rat or in a human. Generally, as discussed herein, an osteoinductive score is assessed based on osteoinductivity in an athymic rat.

"Superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

A "therapeutically effective amount" or "effective amount" is such that when administered, the drug results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response. The dosage administered to a patient can be as single or multiple doses depending upon a variety of factors, including the drugs administered pharmacokinetic properties, the route of administration, patient conditions and characteristics (sex, age, body weight, health, size, etc.), extent of symptoms, concurrent treatments, frequency of treatment and the effect desired.

The terms "treating" and "treatment" when used in connection with a disease or condition refer to executing a protocol that may include osteochondral repair procedure, administering one or more drugs to a patient (human or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient. In some embodiments, the osteoimplant can be used to treat subchondral, osteochondral or condyle, or other bone defects.

Putties according to aspects of the present disclosure will include insoluble collagen fibers, typically from 70% to 100% by weight based on the weight of the total amount of collagen in the osteoimplant. "Soluble collagen" refers to the solubility of individual tropocollagen molecules in acidic aqueous environments. Tropocollagen may be considered the monomeric unit of collagen fibers and its triple helix structure is well recognized. "Insoluble collagen" as used herein refers to collagen that cannot be dissolved in an aqueous alkaline or in any inorganic salt solution without chemical modification, and includes for example insoluble collagen found in hides, splits and other mammalian or reptilian coverings. For example, "natural insoluble collagen" can be derived from the corium, which is the intermediate layer of an animal hide (e.g. bovine, porcine, etc.) that is situated between the grain and the flesh sides. "Reconstituted collagen" is essentially collagen fiber segments that have been depolymerized into individual triple helical molecules, then exposed to solution and then reassembled into fibril-like forms.

Osteoimplant

An osteoimplant for medical uses is provided in various aspects. The osteoimplant comprises, consists essentially of or consists of a plurality of entangled insoluble collagen fibers from 70%, 71%, 72%, 73% 74%, 75%, 76%, 77%, 78%, 79%, 80%, 81%, 82%, 83%, 84%, 85%, 96%, 87%, 88%, 89%, 90%, 91%, 92%, 93%, 94%, 95%, 96%, 97%, 98%, 99% to 100% by weight based on the total weight of the collagen in the osteoimplant. In sonic aspects, the entangled insoluble collagen fibers comprise, consist essentially of, or consist of crosslinked and/or non-crosslinked purified fibrillary collagen.

In other embodiments, the osteoimpla.nt further comprises ceramic granules in an amount from about 0.1%, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 3.9, 4.0, 4.5, 5.0, 5.5, 6.0, 6.5, 7.0, 7.5, 7.8, 8.0, 8.5, 9.0, 9.5, 10, 10.5, 11, 11.5, 12, 12.5, 13, 13.5, 14, 14.5, 15, 15.5, 15.6, 16, 16.5, 17, 17.5, 18, 18.5, 19, 19.5, 20, 20.5, 21, 21.5, 22, 22.5, 23, 23.4, 23.5, 25, 26, 27, 28, 29, 30, 31, 32, 33, 34, 35, 36, 37, 38. 38.5, 39, 39.5, 40, 41, 42, 43, 44, 45, 46, 47, 48, 49, 50 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 to about 85% by weight of an osteoimplant. In some aspects, the ceramic granules usefiil for the osteoimplant of this disclosure comprise, consist essentially of or consist of biphasic calcium phosphate having tricalcium phosphate and hydroxyapatite in a ratio of from about 40:60, 50:50, 55:45, 60:40, 65:35, 70:30, 75:25, 80:20, 85:15, 90:10 to about 95:5. In yet other aspects the ceramic granules have an average particle diameter from about 0.5, 0.6, 0.7, 0.8, 0.9, 1.0, 1.1, 1.2, 1.3, 1.4, 1.5 to 1.6 mm.

In one embodiment, the present application provides a method for making an osteoimplant. The method includes applying a mechanical force to an aqueous slurry of insoluble collagen fibers to cause them to form a plurality of entangled insoluble collagen fibers, which may or may not be crosslinked, mixed with other ingredients, and/or pre-hydrated or lyophilized. The resulting fibrous material is moldable or putty-like and can be used as bone graft substitute for filling osseous voids, promoting fusion of osseous tissues and/or carriers of other ingredients, for example rhBMP-2, other proteins or other additives. The mechanical force used to cause the insoluble collagen to entangle into a fibrous putty-like material can be provided by the turbine blade of a stirring device or any other mechanical method, excluding centrifugthg.

The insoluble collagen entangled polymer material may be combined with additional components to enhance osteo-conductivity and provide compression resistance (e.g. ceramic granules) or improve handling characteristics (e.g. alginate, starch), in some aspects. Further, in other aspects, the insoluble collagen entangled polymer material may be provided in a pre-hydrated, ready-to-use formulation, or may be lyophilized to allow hydration with bone marrow aspirate or a solution containing growth factors.

Figure 1:
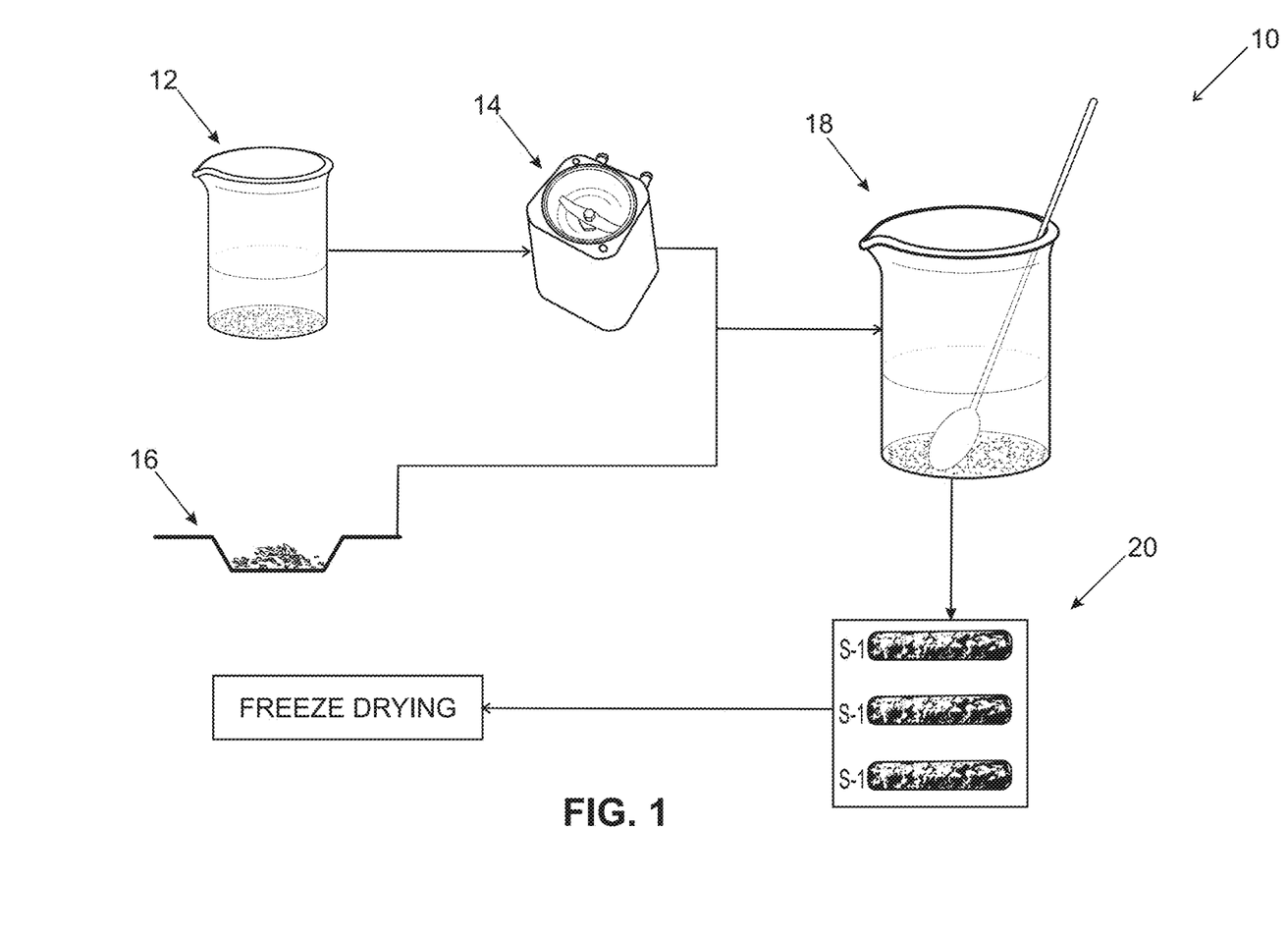
FIG. 1 illustrates the steps of a method for preparing an osteoimplant comprising insoluble collagen entangled polymeric fibers and ceramic granules.

FIG. 1 illustrates an embodiment 10 of a method for preparing an osteoimplant containing insoluble collagen entangled polymeric fibers and ceramic granules. In particular, insoluble purified fibrillary collagen (PFC) blended with water in beaker 12 and subjected to the mechanical force provided by the blade of a mechanical blender 14, such as an IKA blender or other mechanical blender or stirrer, to form a white dense slurry of entangled collagen fibers in beaker 18. The entangled collagen fibers are then mixed with ceramic granules 16 by using simple mixing with a spatula, for example. The resulting homogeneous paste is placed into a mold 20 and further processed by freeze drying to make the osteoimplant.

Figure 2:
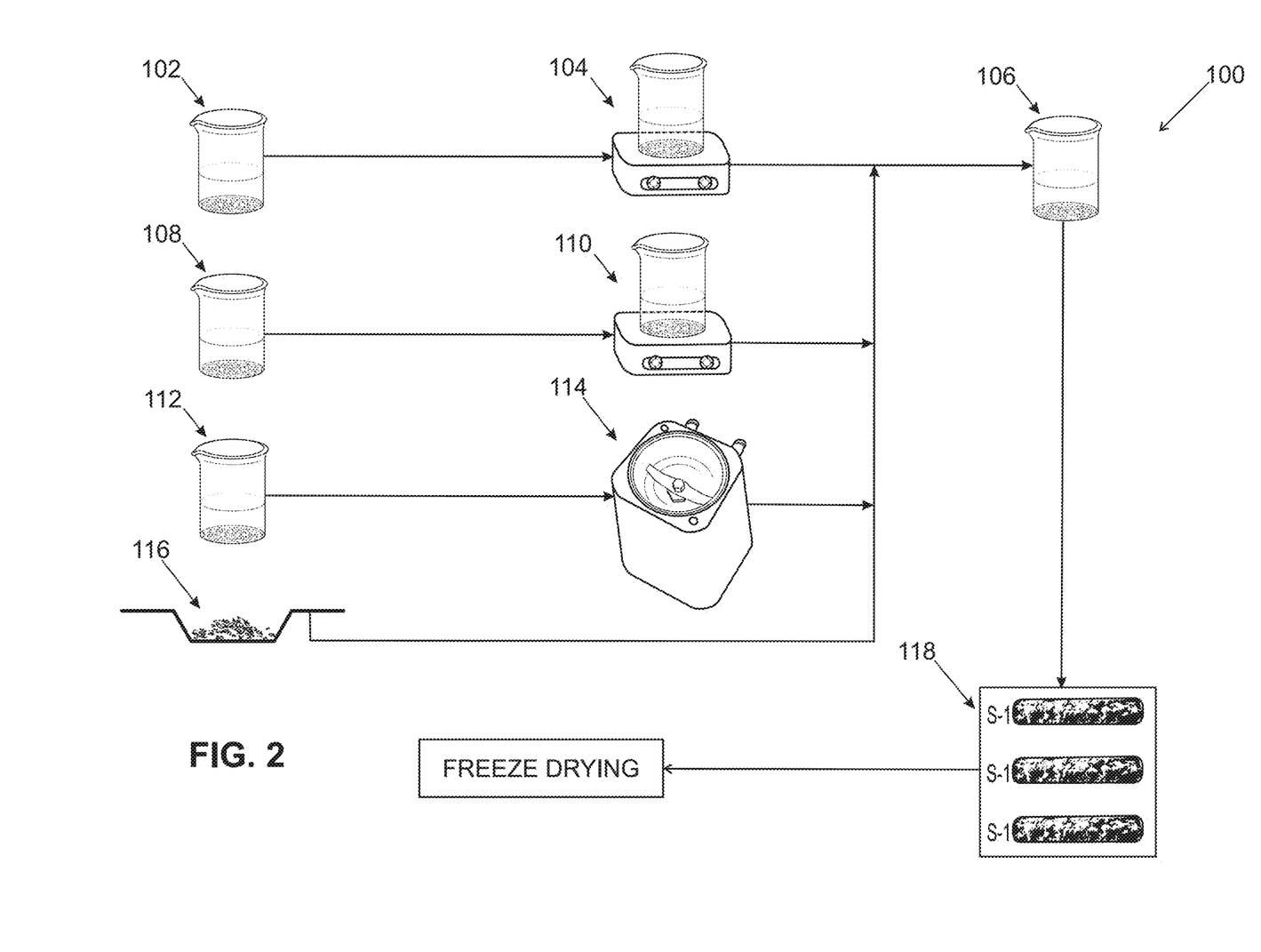
FIG. 2. illustrates the steps of another embodiment of a method for preparing an osteoimplant of insoluble entangled collagen fibers of this application.

FIG. 2 illustrates another embodiment 100 of a method for preparing an osteoimplant containing insoluble entangled collagen fibers of this application. In this method, insoluble purified fibrillary collagen is blended with water in beaker 112, which is subjected to stirring by a magnetic stirrer 114 to form a white dense slurry of entangled collagen fibers in beaker 106. Separately, starch is blended with deionized water in beaker 102 and mixed with a stirrer under heating in beaker 104. Further, polyethylene glycol (PEG) and deionized water solution from beaker 108 are also stirred in beaker 110 and added to the cooled starch gel. The resulting mixture is then added to the slurry of entangled insoluble collagen fibers in beaker 106 and further mixed with ceramic granules 116 to form a homogeneous paste that can be placed into molds 118 for further processing by freeze drying to make the osteoimplant.

In other embodiments, the lyophilized osteoimplant can be further hydrated with a fluid comprising physiologically acceptable water, physiological saline, sodium chloride, dextrose, Lactated Ringer's solution, PBS, blood, bone marrow aspirate, bone marrow fractions or a combination thereof in an amount sufficient to render the osteoimplant moldable.

In yet other embodiments, the osteoimplant comprising entangled insoluble collagen fibers can be pre-hydrated with a fluid comprising physiologically acceptable water, physiological saline, sodium chloride, dextrose, Lactated Ringer's solution, PBS, blood, bone marrow aspirate, bone marrow fractions or a combination thereof in an amount sufficient to provide a ready-to-use formulation which was not lyophilized.

In various aspects, the biodegradable insoluble collagen osteoimplant obtained by the methods of this application comprises, consists essentially of, or consists of macroscopically visible insoluble collagen fiber, namely, collagen fibers visible with the naked eye. The mean length of the collagen fibers is generally from about 3 to about 30 mm, in some embodiments, from about 5 to about 25 trim, and, in other embodiments, from about 7.5 to about 20 mm.

There are many advantages to osteoimplants comprising the entangled insoluble collagen fibers prepared by the methods described herein. It has been unexpectedly found, that these insoluble collagen osteoimplants mimic the natural delivery of many bioactive agents and especially growth factors to a bone defect site. Moreover, these osteoimplants can act as a scaffold for tissue growth and are fully resorbable and/or remodelable and exhibit excellent biocompatibility with bone.

Collagen

The insoluble collagen in the osteoimplant of this application can be derived from any collagen bearing tissue from an animal. The insoluble collagen can be allogenic or xenogenic. The insoluble collagen can be from skin, tendon, fascia, ligament, trachea, or organ collagen. In certain embodiments, the collagen is human collagen or other mammalian collagen (e.g., porcine, bovine, or ovine). The collagen can be sourced from any animal.

If human sourced collagen is used, some of the common processing steps, designed to remove immunogenic proteins, can optionally be skipped. Steps to remove immune proteins typically include treatment with a protolytic enzyme such as papain, or ficin, treatment with a strong oxidizing agent such as sodium chlorate, and exposure to high pH from, for example, sodium hydroxide. If any of these protein destroying steps are to be carried out, they must be completed, and all residual reagents be removed, before the growth factor(s) is added.

Presently, about twenty eight distinct collagen types have been identified in vertebrates, including bovine, ovine, porcine, chicken, marine, and human sources. Generally, the collagen types are numbered by Roman numerals, and the chains found in each collagen type are identified by Arabic numerals. Detailed descriptions of structure and biological functions of the various different types of naturally occurring collagens are generally available in the art.

The collagen may have the same composition as in naturally occurring sources. Examples of sources of collagens include human or non-human (bovine, ovine, and/or porcine), as well as recombinant collagen or combinations thereof. Examples of suitable collagen includes, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XX, human collagen type XXI, human collagen type XXII, human collagen type XVIII, human collagen type XXIV, human collagen type XXV, human collagen type XXVI, human collagen type XXVII, and human collagen type XXVIII, or combinations thereof. Collagen may further or alternatively comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the collagen is all type I or substantially all is collagen type I, namely, at least 60%, at least 65%, at least 70%, at least 75%, at least 80%, at least 85%, at least 90%, or at least 95%. In some embodiments all soft tissue growth factors are conserved. In other embodiments, at least 50%, at least 55%, at least 60%, at least 65%, at least 70%, at least 75%, at least 80% at least 85%, at least 90%, at least 95%, or at least 99% of the tissue growth factors are conserved.

The collagen may be from any collagen containing organ source such as skin, fascia, intestine, tendon, bladder and trachea. In some embodiments, human compatible collagen, and xenograft collagen can be used if they can be rendered non-immunogenic by a process that does not destroy the activity of the natural growth factors contained in the tissue or diminishes the activity by an acceptably small amount. Examples of processes that conserve natural growth factors include but are not limited to glycosidase digestion of carbohydrate moieties of the xenograft, which are optionally followed by treatment of carbohydrate moieties of the xenografts with a capping agent. Thus, sugars and other substances may be removed during processing, while the soft tissue growth factors remain associated with the collagen. In some embodiments soft tissue growth factors are conserved, but any sugars have been removed or at least 50%, at least 55%, at least 60%, at least 65%, at least 70%, at least 75%, at least 80% at least 85%, at least 90%, at least 95%, or at least 99% of them have been removed.

The solid particulate collagen incorporated into the osteoimplant described in this application can be in the form of intact or reconstituted fibers, or randomly-shaped particles, for example. In certain embodiments, the solid particulate collagen will be in the form of particles derived from a sponge material, for example by randomly fragmenting the sponge material by milling, shredding or other similar operations. Such particulated sponge material can have an average maximum particle diameter of less than about 6 mm, more preferably less than about 3 mm, and advantageously in the range of about 0.5 mm to 2 mm. Such materials can, for example, be obtained by milling or grinding a porous sponge material and sieving the milled or round material through a screen having openings sized about 6 mm or smaller, desirably about 0.5 mm to about 2 mm. Retch grinders with associated sieves are suitable for these purposes. The resulting small sponge particles are randomly formed and have generally irregular shapes with remnant structures from the sponge material, and are highly beneficial for use in malleable compositions such as pastes or putties of this application. In this regard, the use of such particulated sponge materials in combination with DBM materials in malleable compositions is considered as an aspect disclosed herein also wherein the sponge material is made all or in part from a bioresorbable material other than collagen. For example, the particulated sponge material can be made from any of the other natural or synthetic polymers disclosed herein.

Likewise, in these particulated sponge embodiments, the liquid carrier can be a polysaccharide-containing substance as disclosed herein or another suitable material, including aqueous and non-aqueous liquid mediums, and the particulated sponge material can optionally be used in the same relative amounts disclosed herein for the collagen solids materials. Further, a sponge starting material has been chemically crosslinked with an aldehyde crosslinker such as formaldehyde or glutaraldehyde, or another suitable chemical crosslinker such as a carbodiimide, or by other techniques such as dehydrothermal or radiation-induced crosslinking, the particulated collagen or other bioresorbable material retains the chemical crosslinking and provides an advantageous, lasting scaffold for bone ingrowth. Other sources of chemically crosslinked, particulate collagen, in fiber form, irregular or other shapes, can also be used to significant advantage, and their use is considered to be another aspect of the present disclosure. These crosslinked particulate materials can be provided as starting materials for preparing compositions as disclosed herein, and therefore as incorporated in the osteoimplant these particles are individually crosslinked. As well, crosslinked solid collagen particles can be used in combination with non-crosslinked collagen in compositions of the present disclosure, wherein the non-crosslinked collagen can be solid (insoluble) or soluble collagen, or combinations thereof. Such crosslinked and non-crosslinked collagen mixtures can be used, for example, to modulate the residence time of the collagen portion of the osteoimplant in vivo.

In other advantageous embodiments, the particulate collagen, crosslinked and/or non-crosslinked, can be in the form of elongate particles, such as fibers. Collagen fibers having a. median width of greater than about 0.2. mm or greater than about 0.5 mm, in certain embodiments with median lengths in the range of about 5 mm to about 20 mm and/or median thicknesses in the range of about 0.02 mm to about 0.2 mm can be used. Illustratively, the collagen fibers can have median widths from about 0.2 mm to about 3 mm (more preferably 0.5 mm to about 3 mm), median lengths of about 5 mm to about 20 mm, and median thicknesses of about 0.02 mm to about 0.2 mm. When such elongate collagen fibers are used, potentially in conjunction with similarly-sized DBM fibers, or other DBM compositions described herein or otherwise, an advantageous mechanical entanglement of materials in the formulation can be achieved.

In various embodiments, the insoluble collagen can be crosslinked, either before or after it is subjected to a mechanical force that causes the insoluble collagen fibers to become entangled into a semi-solid mass. In some embodiments, the use of crosslinked collagen fibers imparts improved characteristics such as: mechanical strength (for example, suturablity, compression, tension) and biodurability (for example, resistant to enzymatic and hydrolytic degradation). Crosslinking may be accomplished using several different crosslinking agents, or techniques (for example, thermal dehydration, EDC, aldehydes (e.g., formaldehyde, gluteraldehyde), natural crosslinking agents such as genipin or proanthocyanidin, and combinations thereof). Each type of crosslinking agent/technique or combinations thereof imparts diverse mechanical and biological properties on the material. These properties are created through the formation of unique chemical bonds that stabilize the insoluble collagen osteoimplant. This stabilization greatly increases the ability of the osteoimplant to hold a shape and conformation, thereby preserving the entangled relationship between the insoluble collagen fibers.

A water-based dispersion or slurry of insoluble collagen can be prepared by an acid treatment. As an example, a dispersion or slurry can include about 0.2 mL of lactic acid in 100 mL of distilled/de-ionized water with about 1.0 g of collagen (e.g., skin, tendon, fascia ligament). In some embodiments, an acidic dispersion or slurry contains from about 0.1 wt % to about 3 wt % collagen, for example, from about 1 wt % (1 g collagen/100 mL solution) and 2 wt % collagen. The collagen particles (e.g., macroscopic fibers, strands) in the dispersion are capable of self-assembly in the absence of a crosslinking agent.

Insoluble collagen has the ability to self-assemble into fibers, and this self-assembly has a significant role in maintaining the structure and the mechanical function of a given tissue. Insoluble collagen self-assembly occurs at physiological pH where the assembled collagen fibers have identifiable quarter staggered configurations with alternating light and dark bands when observed under high magnifications. The regions where the insoluble collagen molecules overlap are the dark banding regions, while the staggered collagen molecules spanning from dark band to dark band are the light banding regions. Within the overlapping region, insoluble collagen molecules are bound together by native cross-links that are formed as part of fiber formation and overall molecule stabilization. Native cross-links alone are not the only element that is maintaining the stability of collagen molecules. Hydrogen bonding between these molecules can be facilitated by water that can also play a role in collagen self-assembly. Water may also continue to influence collagen stability after self-assembly on the micro- and macro-molecular level where water helps to maintain collagen molecular conformation and mechanical properties.

At lower pH, insoluble collagen can disassemble into smaller fibril subunits. This physical transformation is termed swelling in acidic solutions. Without being bound by any particular theory, it is believed that the mechanism is made possible by the charges on the insoluble collagen protein becoming positive, which causes the insoluble collagen fibers to repel each other and deaggregate into subunits because the attractive forces of the interaction between triple helices are eliminated, which can result in a dispersion of insoluble collagen that is homogenous, opalescent, and optically isotropic. In some embodiments, the dispersed or slurried insoluble collagen includes long fibers with diameters in the range of from about 0.05 µm to about 2.5 µm, and lengths from about 5 µm to about 100 µm. In various embodiments, the insoluble collagen fibers are macroscopic, that is they can be seen with the naked eye and their mean length of the collagen fibers is generally from about 3 to about 30 mm, in some embodiments, from about 5 to about 25 mm, and, in other embodiments, from about 7.5 to about 20 mm.

The process of deaggregation is reversible when the insoluble collagen dispersion or slurry is brought to physiological pH with evident collagen fiber assembly, if the acidity of the dispersion or slurry has been maintained above pH 3. As a result, in some embodiments, the pH of the collagen dispersion or slurry ranges from about 3 to about 6.5, for example, from about 3 to about 5, from about 3 to about 4.6, or about 4. As an example, about 0.2 mL of lactic acid in about 100 mL of water provides a pH from about 4 to about 5.

The methods of preparing the osteoimplant compositions involve using different collagen characteristics under different pH conditions to form the compositions. For example, bone particles, DBM or calcium phosphates that are added to the acidic insoluble collagen dispersion slowly neutralize the dispersion or slurry as surface minerals from these sources are dissolved. The gradual rise in pH allows insoluble collagen assembly to take place around the bone particles, which may have exposed insoluble collagen fibers on their surfaces as a result of the mineral dissolution.

In various embodiments, the dispersion or slurry is very pure and the insoluble collagen fibers can slowly be precipitated by drop-by-drop addition of an alkali, such as for example, sodium hydroxide, sodium carbonate, ammonia, sodium sulfate, or the like. Typical pH for this precipitation step is about 7. The insoluble collagen fibers can be filtered or collected by hand.

In various embodiments for the collagen precipitation, the pH of the acidic dispersion of collagen is pH of about 3.5 as a starting point for the precipitation reaction, at about pH of 4.6 transparent shard-like structures form, these structures precipitate out of the acid dispersion at a pH of about 6.0 to about 7.0, where they are transparent, filly formed, firm and stable structures. In various embodiments, the temperature for precipitation is about 20 to about 30° C.

In various embodiments, the insoluble collagen formed is transparent, shard-like structures resembling flexible icicles. The insoluble collagen fibers appear like shard-like gelatin because it is thought that water is trapped within the fiber structure. The insoluble collagen fibers can be de-watered making the fiber structure more textile like and allows further removal of contaminants, such as non-collagenous material, trapped within the water.

In various embodiments, dewatering of the insoluble collagen fibers can be accomplished by, for example, washing with suitable drying agents, air, and/or oven drying. Suitable drying agents include, for example, non-polar solvents such as, for example, acetone, alcohol, or the like. Low temperature drying, such as by air and/or oven at temperatures, for example, of about 35 to about 40° C. can remove any remaining water as the solvents flash off, and can leave substantially pure insoluble collagen in dry firm fiber form.

Particulate Materials

In various embodiments, the osteoimplant (e.g., putty) including a semi-solid mass of entangled insoluble collagen fibers may be combined with additional components which can enhance osteoconductivity and provide compression resistance, such as for example particulate mineral materials and/or DBM.

The mineral materials useful for the osteoimplant described in this disclosure can include a. natural or synthetic mineral or mixture of mineral materials that is effective to provide a scaffold for bone ingrowth. Illustratively, the mineral matrix may be selected from one or more materials from the group consisting of bone particles, Bioglass®, tricalcium phosphate, biphasic calcium phosphate, hydroxyapatite, coralline hydroxyapatite, and biocompatible ceramics. Biphasic calcium phosphate is a useful synthetic ceramic, in some aspects. In various embodiments, such biphasic calcium phosphate can have a tricalcium phosphate: hydroxyapatite weight ratio of about 40:60, 50:50 to about 95:5, about 70:30 to about 95:5, about 80:20, about 85:15 to about 90:10. The mineral material can be particulate having an average particle diameter between about 0.4 and 5.0 mm, between about 0.4 and 3.0 mm, between about 0.4 and 2.0 mm, between 0.5 and 1.6 mm.

In various embodiments, calcium phosphates can be obtained from calcium phosphate ceramics. Examples of such calcium phosphate ceramics include calcium phosphate compounds and salts, and combinations thereof, including: tricalcium phosphate $Ca_3(PO_4)_2$ (TCP), including alpha-TCP, beta-TCP, and biphasic calcium phosphate containing alpha- and beta-TCP; amorphous calcium phosphate (ACP); monocalcium phosphate $Ca(H_2PO_4)_2$ (MCP) and monocalcium phosphate monohydrate $Ca(H_2PO_4)_2 \cdot H_2O$ (MCPM); dicalcium phosphate $CaHPO_4$ (DCP) and dicalcium phosphate dihydrate $CaHPO_4 \cdot 2H_2O$ (DCPD); tetracalcium phosphate $Ca_4(PO_4)_2O$ (TTCP); octacalcium phosphate $Ca_8H_2(PO_4)_6 \cdot 5H_2O$ (OCP); calcium hydroxyapatite $Ca_{10}(PO_4)_6(OH)_2$ (CHA); calcium oxyapatite $Ca_{10}(PO_4)_6O$ (COXA); calcium carbonate apatite $Ca_{10}(PO_4)_6CO_3$ (CCA); calcium carbonate hydroxyapatites, $Ca_{10}(PO_4)_5(OH)(CO_3)_2$ or $Ca_{10}(PO_4)_4(OH)_2(CO_3)_3$ (CCHA) or a combination thereof.

Calcium phosphates useful herein also include calcium-deficient calcium phosphates in which the molar or mass ratio of Ca:P is reduced by about 20% or less, preferably about 15% or less, preferably about 10% or less, relative to the corresponding calcium non-deficient species, examples of which include calcium-deficient hydroxyapatites, e.g., $Ca_{10}-X(HPO_4)_X(PO_4)_{6-X}(OH)_{2-X}$ ($0 \leq X \leq 1$) (CDHA); calcium-deficient carbonate hydroxyapatites (CDCHA); calcium-deficient carbonate apatites (CDCA); and other calcium phosphate compounds and salts known as useful in the bone graft material field, e.g., calcium polyphosphates and calcium-, phosphate-, and/or hydroxyl-"replaced" calcium phosphates, as further described below.

Calcium-replaced calcium phosphates are also useful herein, including homologs of any of the above in which some of, preferably a minority of (preferably about or less than: 40%, 35%, 33.3%, 30%, 25%, 20%, 15%, or 10% of) the calciums are substituted with monovalent and/or divalent metal cation(s), e.g., sodium calcium homologs thereof, such as $CaNa(PO_4)$.

Phosphate-replaced calcium phosphates are also useful herein, including homologs of any of the above in which some of, preferably a minority of (preferably about or less than: 40%, 35%, 33.3%, 30%, 25%, 20%, 15%, or 10% of) the phosphate groups are substituted with carbonate, hydrogen phosphate, and/or silicate groups.

In another aspect of the disclosure, the mineral material can include bone particles, possibly cancellous but preferably cortical, ground to provide an average particle diameter among those discussed above for the particulate mineral material. Both human and non-human sources of bone are suitable for use in the instant disclosure, and the bone may be autograft, allograft or xenograft in nature relative to the mammal to receive the implant. Appropriate pre-treatments known in the art may be used to minimize the risks of disease transmission and/or immunogenic reaction when using bone particles as or in the mineral material. Such bone particles can be used alone or in combination with synthetic mineral materials as described herein.

In one embodiment, xenogenic bone that has been pre-treated to reduce or remove its immunogenicity is used in or as the porous mineral matrix in the implant composition, For example, the bone can be calcined or deproteinized to reduce the risks of immunogenic reactions to the implant material.

DBM can be produced by acid extraction, thermal freezing, irradiation, or physical extraction of inorganic minerals from human or animal bone. The moisture level of the demineralized bone matrix can be easily controlled by air-drying or freeze-drying. Air dried demineralized bone matrix can include greater than about 10 weight percent of moisture, while in certain circumstances, freeze dried demineralized bone matrix can include less than about 6 weight percent of moisture. In some aspects, DBM can include between about 5 and about 30 weight percent (e.g., between about 5-20 weight percent, between about 10-15 weight percent, or between about 10-12 weight percent, or between about 5-10 weight percent) of moisture, e.g., water. In various embodiments, the demineralized bone matrix includes greater than or equal to about 6, 10, 12, 14, 16, 18, 20, 22, 24, 26, or 28 weight percent of moisture; and/or less than or equal to about 30, 28, 26, 24, 22, 20, 18, 16, 14, 12, or 6 weight percent of moisture. In some embodiments, the bone used to manufacture the demineralized bone matrix can be cortical, cancellous, cortico-cancellous of autogenous, allogeneic, xenogeneic or transgenic in origin.

In various embodiments of the present teachings, demineralized bone matrix can be supplied as powdered cortical or cancellous bone or dry chips ranging in size from about 10 μm to about 10 mm, from about 50 μm to about 5 mm, from about 100 μm to about 1 mm, from about 150 μm to about 0.8 mm, or from about 200 μm to about 0.75 mm.

In some embodiments, the osteoimplant can have fully demineralized bone fibers in combination with surface demineralized bone chips, where the chips to fibers ratio is about 90:10, 80:20, 70:30, 60:40, 50:50, 40:60, 30:70, 20:80 and/or 10:90. In various embodiments, a surface demineralized bone chips to fibers ratio is about 90:10, 80:20, 70:30, 60:40, 50:50, 40:60, 30:70, 20:80 and/or 10:90 that can be used in the device. In some embodiments, a surface demineralized chips to fully demineralized fibers ratio is about 90:10, 80:20, 70:30, 60:40, 50:50, 40:60, 30:70, 20:80 and/or 10:90 that can be used in the osteoimplant.

In some embodiments, the osteoimplant can comprise bone fibers. The bone fibers can be elongated and have a diameter or average width of, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In one embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

Polysaccharides

Polysaccharides that can be used in combination with the entangled insoluble collagen fibers to provide additional toughness and improve the cohesiveness of the resulting osteoimplant. Useful polysaccharides include, for example, alginate, hyaluronic acid, chondroitin sulfate, dextran, dextran sulfate, heparin, heparin sulfate, chitosan, gellan gum, xanthan gum, guar gum, and K-carrageenan, starch (e.g. potato starch, wheat starch, or corn starch), or mixtures of two or more of these or other polysaccharides. The gel-forming agent can also be a gel-forming polypeptide, including thermally reversible gel forming polypeptides such as gelatin. In certain embodiments, gelatin or another thermally reversible gel forming agent that has a gel temperature at or slightly above human body temperature (about 37° C.) can be used in addition to or as an alternative to the polysaccharide compound(s).

In various embodiments, starch useful as an additive to the implantable putty described in this application includes potato starch for electrophoresis, corn starch, waxy corn starch, "unmodified" wheat starch, "purified" wheat starch and potato starch, all easily available from commercial sources.

In certain embodiments, alginate polymers can also be used in combination with the entangled insoluble collagen fibers to provide additional toughness and improve the cohesiveness of the resulting osteoimplant (e.g., putty). In various embodiments, useful alginates may have average molecular weights ranging from 2 to 1000 kilodaltons (W). The molecular weight of alginates can affect the properties of the moldable composition. Generally, lower molecular weight alginates will be more biodegradable. In some embodiments, the alginate polymers have an average molecule weight of from 5 to 350 kD. In other embodiments, the alginate polymers have an average molecule weight of from 2 to 100 kD. In yet other embodiments, the alginate polymers have an average molecule weight of from 50 to 500 kD. In some embodiments, the alginate polymers have an average molecule weight of from 100 to 1000 kD. The molecular weights identified in this paragraph can similarly apply to other polysaccharides when used with the osteoimplant (e.g., putty) described in this application. The alginate, when used, may possess a viscosity in a 1% solution measured at 20° C. of from 25 to 1000 mPas and in some embodiments, 50 to 1000 mPas (1% solution, 20° C.).

Other Additives

In various aspects, an additive such as starch may result in inducing long hydration times for the starch containing insoluble collagen osteoimplant of this disclosure. Other additives, such as polyethylene glycol (PEG) can be added to the starch containing osteoimplant (e.g., putty) to enhance hydration time.

As a polyol compound, polyethylene glycol polymer can have a molecular weight of less than about 10,000, for example, in the range of about 500 to about 5000 in certain embodiments. Such a hydrating or wetting agent can constitute about 0.01% to about 1.5% by weight of the implant body on a dry weight basis. Especially in the case of relatively hydrophobic polysaccharides that resist wetting, such as alginates, it has been found that the incorporation of a biocompatible wetting agent significantly enhances the formation of a moldable material by adding an aqueous medium to a dried implant body or other dry material as described herein. Dried implant bodies that include a mixture of starch and alginate have also been found to wet more readily than those with alginate alone, and can optionally include a mixture of all three of a starch, an alginate, and a biocompatible wetting agent as described above.

If desired, the insoluble collagen osteoimplant of this application can be modified in other ways. Any useful biological substance that is water soluble or at least hydrophilic can be added alone or in combination to the entangled insoluble collagen fibers as described above. The insoluble collagen should bind to one or more of the sites of hydration on the water-soluble or hydrophilic material, and so displace the water. If the material is not naturally water soluble or hydrophilic, it can be derivatized or otherwise be made water-soluble or hydrophilic before being combined with the collagen system. Types of useful water soluble/hydrophilic substances include, for example, antibiotics, pain relievers, growth factors, anti-inflammatories.

Medically and/or surgically useful substances which can be readily combined with the implantable composition of this application include, for example, antiviricides, particularly those effective against and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentarnycin; amino acids, peptides, vitamins, inorganic elements, inorganic compounds, cofactors for protein synthesis, homones; endocrine tissue or tissue fragments; synthesizers; enzymes such as collagenase, peptidases, oxidases; polymer cell scaffolds with paraenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1) (IGF-2), platelet derived growth factor (PDGF), fibroblast growth factors (FGF), vascular endothelial growth factor (VEGF), angiogenic agents, bone promoters, cytokines, interleukins, genetic material, genes encoding bone promoting action, cells containing genes encoding bone promoting action; growth hormones such as somatotropin; bone digesters; antitumor agents; fibronectin; cellular attractants and attachment agents; immunosuppressants; permeation enhancers, for example, fatty acid esters such as laureate, myristate and stearate monesters of polyethylene glycol, surface active agents, enamine derivatives, α-keto aldehydes; nucleic acids; epidermal growth factor (EGF); all collagen types (not just type 1); non-collagenous proteins such as osteopontin, osteonectine, bone sialo proteins, vitronectin, thrombospondin, proteoglycans, decorin, biglycan, aggrecan, versican, tenascin, matrix gla protein, hyaluronan; soluble and insoluble components of the immune system, soluble and insoluble receptors including truncated forms, soluble, insoluble and cell surface bound ligands including truncated forms; chemokines, bioactive compounds that are endocytosed; compounds capable of altering the membrane potential of cells, compounds capable of altering the monovalent and divalent cation/anion channels of cells; bone resorption inhibitors and stimulators; angiogenic and mitogenic factors; bioactive factors that inhibit and stimulate second messenger molecules; integrin adhesion molecules; clotting factors; externally expanded autograft or xenograft cells and any combinations thereof.

Growth Factors

In many aspects, the insoluble collagen osteoimplant described in this application can be used to deliver growth factors to the site of an osseous tissue. The growth factors include osteoinductive agents (e.g., agents that cause new bone growth in an area where there was none) and/or osteoconductive agents (e.g., agents that cause ingrowth of cells) and also fibrous or soft tissue inducing agents. Osteoinductive agents can be polypeptides or polynucleotide compositions. Polynucleotide compositions of the osteoinductive agents include, but are not limited to, isolated Bone Morphogenic Protein (BMP), Vascular Endothelial Growth Factor (VEGF), Connective Tissue Growth Factor (CTGF, which may be specific for tendons and ligaments), Osteoprotegerin, Growth Differentiation Factors (GDFs), Cartilage Derived Morphogenic Proteins (CDMPs, which can be a foundation for soft or hard tissue), Lim Mineralization Proteins (LMPs), Platelet derived growth factor, (PDGF or rhPDGF, which is particularly advantageous for use with soft tissue), Insulin-like growth factor (IGF) or Transforming Growth Factor beta (TGF-beta) polynucleotides.

The insoluble collagen osteoitnplant may also comprise one or more additional growth factors, including but not limited to BMP-2, rhBMP12 or BMP7. These additional growth factors, unlike the conserved proteins are ones that have been added to the collagen during a subsequent processing step. The identity of proteins may be the same as or different than the conserved proteins. In some embodiments the collagen may be treated so that it also binds to these additional proteins. In other embodiments, these additional proteins are not bound to the entangled insoluble collagen fibers, but are loosely associated with them. In some embodiments, the resulting concentration of growth factors is from 10% to 30% greater than in the natural state or from 30% to 50% greater than in the natural state or from 50% to 70% greater than in the natural state.

Additional growth factors can include polynucleotide compositions. Polynucleotide compositions include, but are not limited to, gene therapy vectors harboring polynucleotides encoding the osteoinductive polypeptide of interest. Gene therapy methods often utilize a polynucleotide that codes for the osteoinductive polypeptide operatively linked to or associated with a promoter or any other genetic elements necessary for the expression of the osteoinductive polypeptide by the target tissue. Such gene therapy and delivery techniques are known in the art (see, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, to promote or to facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art General methods are described, for example, in U.S. Pat. Nos. 5,593,972, 5,589,466, and 5,580,859, the disclosures of which are herein incorporated by reference in their entireties. Gene therapy vectors further comprise suitable adeno-viral vectors including, but not limited to, for example, those described in U.S. Pat. No. 5,652,224, which is herein incorporated by reference.

Additional growth factors also include, but are not limited to, isolated polynucleotides that encode Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents also include, but are not limited to, full length proteins, fragments or variants thereof.

Variants of the isolated osteoinductive agents include, but are not limited to, polypeptide variants that are designed to increase the duration of activity of the osteoinductive agent in vivo. Typically, variant osteoinductive agents include, but are not limited to, frill length proteins or fragments thereof that are conjugated to polyethylene glycol (PEG) moieties to increase their half-life in vivo (also known as pegylation). Methods of pegylating polypeptides are well known in the art (See, e, U.S. Pat. No. 6,552,170 and European Pat. No. 0,401,384 as examples of methods of generating pegylated polypeptides), In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fe portion of human Immunoglobulin G (IgG). Methods of making fusion proteins and constructs encoding the same are well known in the art.

Isolated osteoinductive agents that may be included within the insoluble collagen osteoimplant are typically sterile. In a non-limiting method, sterility is readily accomplished for example by filtration through sterile filtration membranes (e.g., 0.2 micron membranes or filters). In one embodiment, the insoluble collagen osteoimplant includes osteoinductive agents comprising one or more members of the family of Bone Morphogenic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same. In one embodiment, the at least one bone morphogenic protein is BMP-2.

BMPs utilized as osteoinductive agents may comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents that are included in the insoluble collagen osteoimplant include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors that can be loaded in the insoluble collagen osteoimplant further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat, No, 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313, 119 (herein incorporated by reference in its entirety), or acylguanidine compounds such as those described in U.S. Pat. No. 6,492,356 (herein incorporated by reference in its entirety).

In another embodiment, isolated osteoinductive agents that can be loaded in the insoluble collagen osteoimplant include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents that can be loaded in the insoluble collagen osteoimplant include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents that can be loaded in the insoluble collagen osteoimplant include one or more members of the family of Transforming Growth Factor-beta ("TGF-betas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents that can be loaded in the insoluble collagen osteoimplant include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH-69643, or AAH-74921, as well as mature GDF-2 polypeptides or polynucleotides encoding the same. GDF-3 polynucleotides or polypeptides corresponding to GenBank Accession Numbers AF263538, BCO30959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BCO28237 or AAH28237, as well as mature GDF-10 polypeptides or polynucleotides encoding the same. GDF-11 polynucleotides or polypeptides corresponding to GenBank Accession Numbers AF100907, NP_005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP_004855, as well as mature GDF-15 polypeptides or polynucleotides encoding the same.

In another embodiment, isolated osteoinductive agents that can be loaded in the insoluble collagen osteoirnplant include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents that can be loaded in the insoluble collagen osteoimplant include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents that can be loaded in the matrix include one or more members of any one of the families of Bone Morphogenic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), as well as mixtures or combinations thereof.

In another embodiment, the one or more isolated osteoinductive agents that can be loaded in the insoluble collagen osteoimplant are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and/or any combination thereof; Osteoprotegerin; TGF-beta-1, TGF-beta-2, TGF-beta-3, or any combination thereof; or any combination of one or more members of these groups.

Formation of Osteoimplant

The insoluble collagen osteoimplant containing a bioactive agent provided herein may be used to form the osteoimplant for implanting in a bone cavity. The osteoimplant resulting from the mixture of the insoluble collagen and/or bioactive agent, DBM, additive, may be flowable, have a putty consistency, may be shaped or molded, and/or may be deformable but it will not harden. The osteoimplant may assume a determined or regular form or configuration such as a sheet, plate, disk, tunnel, cone, or tube, to name but a few. Prefabricated geometry may include, but is not limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the osteoimplant. Such plates may include such conformations as, e.g., concave contoured, bowl shaped, or detect shaped. The osteoimplant can be machined or shaped by any suitable mechanical shaping means. Computerized modeling can provide for the intricately-shaped three-dimensional architecture of an osteoimplant custom-fitted to the bone repair site with great precision. In embodiments wherein the osteoimplant is shaped or moldable, the implant may retain coherence in fluids.

Accordingly, the insoluble collagen may be subjected to a configuring step to form an osteoimplant. The configuring step can be employed using conventional equipment known to those skilled in the art to produce a wide variety of geometries, e.g., concave or convex surfaces, stepped surfaces, cylindrical dowels, wedges, blocks, screws, and the like. Also useful are demineralized bone and other matrix preparations comprising additives or carriers such as binders, fillers, plasticizers, wetting agents, surface active agents, biostatic agents, biocidal agents, or the like. Some exemplary additives and carriers include polyhydroxy compounds, polysaccharides, glycosaminoglycan proteins, nucleic acids, polymers, polaxomers, resins, clays, calcium salts, and/or derivatives thereof.

In some embodiments, the insoluble collagen osteoimplant prepared from a mixture of collagen slurry and bioactive agent and DBM may be placed in a containment device such as a porous mesh to provide a delivery system. In various embodiments, the device may comprise a. polymer (such as polyaklenes (e.g., polyethylenes, polypropylenes, etc.), polyamides, polyesters, polyurethanes, poly(lactic acid-glycolic acid), poly(lactic acid), poly(glycolic acid), poly(glaxanone), poly(orthoesters), poly(pyrolicacid), poly (phosphazenes), L-co-G, etc.), other bioabsorbable polymer such as Dacron or other known surgical plastics, a natural biologically derived material such as collagen, a ceramic (with bone-growth enhancers, hydroxyapatite, etc.), PEEK (polyether-etherketone), dessicated biodegradable material, metal, composite materials, a biocompatible textile (e.g., cotton, silk, linen), or other. In one embodiment, the containment device is formed as a long bag-like device and may be used with minimally invasive techniques.

To facilitate on-site preparation and/or usage of the insoluble collagen osteoimplant herein, the bioactive agent such as a growth factor, preferably in lyophilized or frozen form, and the collagen slurry, can be stored in separate packages or containers under sterile conditions and brought together in intimate admixture at the moment of use for immediate application to an osseous defect site employing any suitable means such as spatula, forceps, syringe, tamping device, and the like. Alternatively, the insoluble collagen bioactive agent containing osteoimplant can be prepared well in advance, lyophilized or otherwise dried and stored under sterile conditions until required for use. In some embodiments, the insoluble collagen osteoimplant described herein can be combined with autograft bone marrow aspirate, autograft bone, preparations of selected autograft cells, autograft cells containing genes encoding bone promoting action prior to being placed in a defect site. In various embodiments, the implant composition is packaged already mixed and ready for use in a suitable container, such as for example, syringe, resealable non-toxic bottle, a bag mesh or pouch or is provided as a kit which can be prepared at a surgeon's direction when needed.

Having now generally described the invention, the same may be more readily understood through the following reference to the following examples, which are provided by way of illustration and are not intended to limit the present invention unless specified.

EXAMPLES

Example 1

In this example, an osteoimplant (e.g., composite) containing insoluble collagen fibers and ceramic granules was prepared to be used as a bone graft substitute for filling osseous voids and promoting the fusion of osseous tissues. The ceramic granules were added to provide enhanced osteconductivity and compression resistance.

6.2 g of insoluble purified fibrillary collagen (PFC) was blended with 40 ml of water for 20 seconds in an IKA blender until a white dense slurry of entangled collagen fibers was obtained. 18.4 g granules of biphasic calcium phosphate (BCP) were added to the PFC slurry and mixed with a spatula to obtain a homogeneous mixture.

The resulting homogeneous mixture was placed into an aluminum mold of 1 by 1 by 5 cm as illustrated in FIG. 1. The mold was then inserted into a freeze dryer for 3 days. The temperature of the plate was pre-frozen for 4 hours at "maximum cold," then the temperature was changed to −20° C. at 2° C./min where it remained for 24 hours. Thereafter the temperature was raised to −5° C. for 32 hours. Finally, the temperature was raised to 21° C. at 1° C./min.

Figure 3:
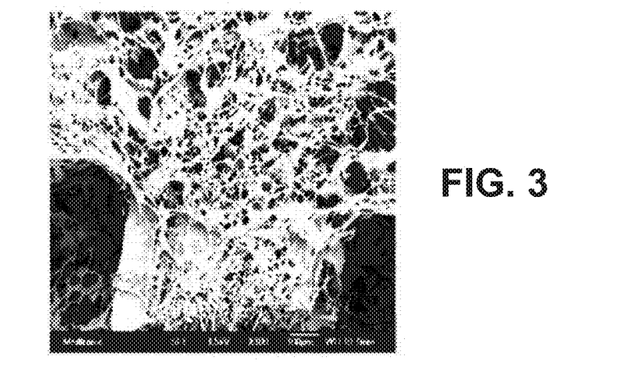
FIG. 3, FIG. 4 and FIG. 5 illustrate scanning electron microscope (SEM) images of the putty like osteoimplants of this disclosure obtained after freeze drying, provided at 100 times magnification (FIGS. 3 and 4) and 2000 time magnification (FIG. 5), It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.
Figure 4:
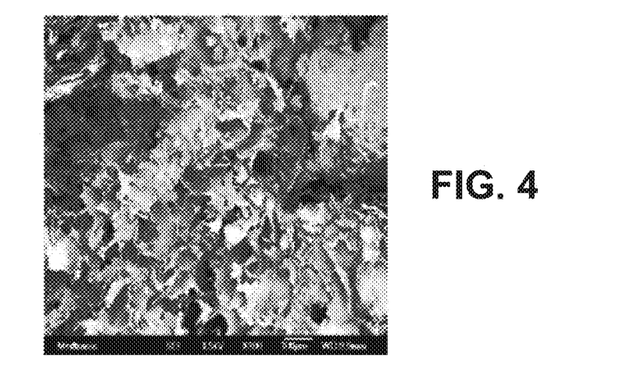
Figure 5:
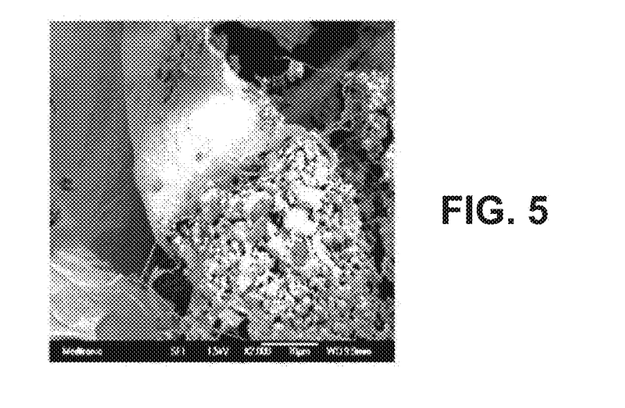

FIGS. 3-5 illustrate images of the putty like osteoimplant obtained after freeze drying provided by scanning electron microscope (SEM) at 100 times magnification (FIGS. 3 and 4) and 2000 time magnification (FIG. 5) In particular, FIG. 3 is an SEM evaluation taken of the bottom portion of the freeze dried osteoimplant of this example at 100 times magnification. FIG. 4 is an SEM evaluation of a through-cut portion of the freeze dried osteoimplant of this example at 100 times magnification. FIG. 5 is an SEM evaluation of a through-cut portion of the freeze dried osteoimplant of this example at 2000 times magnification.

Example 2

In this example, the osteoimplant of insoluble collagen fibers and ceramic granules also contained additional components provided to improve handling characteristics, for example, hydration time by adding starch and polyethylene glycol (PEG).

3.1 g of insoluble purified fibrillary collagen (PFC) was blended with 20 ml of water for 20 seconds in an IKA blender until a white dense slurry was obtained. Separately, 3.1 g of potato starch for electrolysis was added to a 10 ml of deionized water, placed into a thermostatted water bath and heated to 80° C. for 5 minutes. After the resulting starch solution was cooled, 0.37 g polyethylene glycol (PEG) dissolved in 5 ml of deionized water were added to the cooled starch gel. The PFC slurry was added to the starch/PEG gel. 18.4 g granules of biphasic calcium phosphate (BCP) were added to the PFC/starchPEG slurry and mixed with a spatula to obtain a homogeneous mixture. The composition containing insoluble collagen fibers of this example yielded an osteoimplant having a density of 0.70 g/cc as summarized below in Table 1, below:

TABLE 1

| Components | Potato Starch | PFC | BCP | PEG | Density |
|---|---|---|---|---|---|
| Quantity | 12.5% | 12.5% | 75% | 1.5% in addition to the total weight | 0.7 |

The above homogeneous mixture was placed into an aluminum mold of 1 by 1 by 5 cc as illustrated in FIG. 2. The mold was then inserted into a freeze dryer for 3 days. The temperature of the plate was pre-frozen for 4 hours at "maximum cold," then the temperature was changed to −20° C. at 2° C./min where it remained for 24 hours. Thereafter the temperature was raised to −5° C. for 32 hours, Finally, the temperature was raised to 21° C. at 1° C./min.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for making an osteoimplant, the method comprising: applying a mechanical force using a grinder or a blender to an aqueous slurry of insoluble collagen fibers to entangle the insoluble collagen fibers so as to form a semi-solid mass of entangled insoluble collagen fibers, the aqueous slurry of insoluble collagen fibers being purified fibrillary collagen; mixing the semi-solid mass of entangled collagen fibers with a gel comprising starch or alginate, and polyethylene glycol (PEG) and deionized water to form a mixture; mixing the mixture with ceramic granules having biphasic calcium phosphate comprising tricalcium phosphate and hydroxyapatite in a ratio from about 40:60 to about 95:5; placing the mixture in a mold; and lyophilizing the mixture to form the osteoimplant by placing the mold in a freeze dryer; wherein the method comprises mixing PEG in deionized water with the gel to form a solution before adding the slurry to form the mixture; and then adding the biphasic calcium phosphate to the mixture.

2. A method of claim 1, further comprising crosslinking the insoluble collagen fibers of the semi-solid mass prior to lyophilization.

3. A method of claim 1, wherein the ceramic granules have an average particle diameter in the range from about 0.5 to about 1.6 mm.

4. A method of claim 3, wherein the amount of biphasic calcium phosphate is in a range from about 1% to about 85% by weight based on the total weight of the osteoimplant.

5. A method of claim 1, wherein the osteoimplant comprises starch or alginate in an amount from about 0.1% to about 12.5% by weight based on the total weight of the osteoimplant, and the polyethylene glycol (PEG) in an amount comprising 1.5% by weight based on the total weight of the osteoimplant.

6. A method of claim 1, wherein the insoluble collagen fibers are purified fibrillary collagen in an amount from about 1% to about 40% by weight based on the total weight of the osteoimplant.

7. A method of claim 6, wherein the osteoimplant has a density of about 0.7 g/cc.

8. A method of claim 1, wherein the lyophilization comprises changing the temperature of the freeze dryer to −20° C. at 2° C./min; then maintaining the temperature at −20° C. for 24 hours; then raising the temperature to −5° C.; then maintaining the temperature at −5° C. for 32 hours; and then raising the temperature to 21° C. at 1° C./min.

9. A method of claim 1, wherein the osteoimplant has a density of 0.70 g/cc and the osteoimplant comprises about 12.5 wt. % of starch or alginate, about 12.5 wt. % of insoluble purified fibrillary collagen, about 75 wt. % of biphasic calcium phosphate and about 1.5 wt. % PEG.

* * * * *